US011166750B1

(12) United States Patent
Wurapa

(10) Patent No.: US 11,166,750 B1
(45) Date of Patent: Nov. 9, 2021

(54) MONOPLANAR DEVICE FOR STABILIZING AND DISTRACTING AN ANATOMICAL JOINT

(71) Applicant: Raymond K. Wurapa, Blacklick, OH (US)

(72) Inventor: Raymond K. Wurapa, Blacklick, OH (US)

(73) Assignee: Raymond K. Wurapa, Blacklick, OH (US)

( * ) Notice: Subject to any disclaimer, the term of this patent is extended or adjusted under 35 U.S.C. 154(b) by 0 days.

(21) Appl. No.: 17/319,149

(22) Filed: May 13, 2021

(51) Int. Cl.
*A61B 17/64* (2006.01)

(52) U.S. Cl.
CPC ...... *A61B 17/6458* (2013.01); *A61B 17/6416* (2013.01); *A61B 17/6491* (2013.01)

(58) Field of Classification Search
CPC ..... A61B 17/60; A61B 17/64; A61B 17/6416; A61B 17/6425; A61B 17/6458; A61B 17/6466; A61B 17/6491; A61B 17/66; A61B 17/68; A61B 2017/681
USPC ..................................................... 606/54, 57
See application file for complete search history.

(56) References Cited

U.S. PATENT DOCUMENTS

| | | |
|---|---|---|
| 4,628,919 A | 12/1986 | Clyburn |
| 5,152,280 A | 10/1992 | Danieli |
| 5,167,661 A | 12/1992 | Wagenknecht |
| 5,304,177 A | 4/1994 | Pennig |
| 5,941,877 A | 8/1999 | Viegas et al. |
| 5,976,125 A | 11/1999 | Graham |
| 6,162,223 A | 12/2000 | Orsak et al. |
| 7,507,240 B2 | 3/2009 | Olsen |
| 9,750,538 B2 | 9/2017 | Soffiatti et al. |
| 9,867,637 B2 | 1/2018 | Sanders et al. |
| 10,973,550 B2 * | 4/2021 | Wurapa .............. A61B 17/6416 |

OTHER PUBLICATIONS

Mikai Complete System, 2016 Mikai S.p.A., www.mikai.us/medical-surgery-devices.

* cited by examiner

*Primary Examiner* — Eduardo C Robert
*Assistant Examiner* — Christina Negrellirodriguez
(74) *Attorney, Agent, or Firm* — McNees Wallace & Nurick LLC

(57) ABSTRACT

A monoplanar device for stabilizing and distracting an anatomical joint is disclosed including first and second shafts having engagement features that form a hinge joint with a single axis of rotation, the shafts being constrained by the hinge joint to move relative to one another only around the single axis of the hinge joint. The shafts and the hinge joint are disposed in a single plane with the single axis being about orthogonal thereto. A first clamp having a recess and a pin hole is slidingly disposed on the first shaft, and a second clamp having a pin hole is slidingly disposed on the second shaft. The pin holes are arranged to receive bone pins for insertion into bones adjacent to the anatomical joint. A distraction screw disposed between a threaded partial bore of the first shaft and the recess rotates to advance the first clamp along the first shaft.

20 Claims, 7 Drawing Sheets

MONOPLANAR DEVICE FOR STABILIZING AND DISTRACTING AN ANATOMICAL JOINT

FIELD OF THE INVENTION

The disclosure relates generally to a medical device for fixation and distraction of joint dislocations and fractures. In some particular embodiments, the medical device is useful for dislocations, fractures, and comminuted fractures of the proximal interphalangeal joint.

BACKGROUND OF THE INVENTION

Injuries to joints present a variety of challenges, including achieving controlled distraction and fixation and preserving motion of the joint during healing. For example, joints of the digits of a human hand are commonly injured during day-to-day activities. Existing solutions for fixing the bones, in particular for the commonly injured bones of the proximal interphalangeal joint, are bulky, imprecise with respect to distraction, and do not provide for natural flexion and extension.

Recent advances in medical devices for fixation and distraction of joint dislocations and fractures are disclosed in U.S. Pat. No. 10,973,550, entitled "Monoplanar Hinged Adjustable External Fixator for Bone Fixation and Distraction," used on Apr. 13, 2021, the disclosure of which are hereby incorporated by referenced as if fully recited herein.

There exists a need for distraction and fixation solutions that provide a hinged design based on the native joint axis to allow more anatomic mobilization of an affected joint and with minimal bulk to improve patient tolerance.

BRIEF DESCRIPTION OF THE INVENTION

In an exemplary embodiment, a monoplanar device for stabilizing and distracting an anatomical joint includes a first shaft, a second shaft, a first clamp, a second clamp, and a distraction screw. The first shaft includes a first engagement feature disposed at a first end of the first shaft and a threaded partial bore disposed along the first shaft. The second shaft includes a second engagement feature disposed at a first end of the second shaft. The first clamp is slidingly disposed on the first shaft, the first clamp including a recess and a first pin hole arranged to receive a first bone pin for insertion into a first bone adjacent to the anatomical joint. The second clamp is slidingly disposed on the second shaft, the second clamp including a second pin hole arranged to receive a second bone pin for insertion into a second bone adjacent to the anatomical joint. The distraction screw is disposed between the threaded partial bore and the recess such that the distraction screw is threadedly engaged with the threaded partial bore and axially and radially retained by the recess. The first engagement feature cooperates with the second engagement feature to form a hinge joint with a single axis of rotation connecting the first shaft to the second shaft, the first shaft and the second shaft being constrained by the hinge joint to move relative to one another only around the single axis of rotation of the hinge joint. The first shaft, the second shaft, and the hinge joint are disposed in a single plane with the single axis of rotation of the hinge joint being about orthogonal to the single plane. The first pin hole is aligned to receive the first bone pin about orthogonal to the single plane such that the first bone pin is aligned about parallel to the single axis of rotation of the hinge joint. The second pin hole is aligned to receive the second bone pin about orthogonal to the single plane such that the second bone pin is aligned about parallel to the single axis of rotation of the hinge joint and the first bone pin. Clockwise rotation of the distraction screw advances the first clamp along the first shaft in a first direction and counterclockwise rotation of the distraction screw advanced the first clamp along the first shaft opposite to the first direction.

In another exemplary embodiment, a monoplanar device for stabilizing and distracting an anatomical joint includes a first shaft, a second shaft, a first clamp, a first bone pin, a second clamp, a second bone pin, a distraction screw, and a reversible lock. The first shaft includes a first engagement feature disposed at a first end of the first shaft and a threaded partial bore disposed along the first shaft. The second shaft includes a second engagement feature disposed at a first end of the second shaft. The first clamp is slidingly disposed on the first shaft, the first clamp including a recess and a first pin hole. The first bone pin is disposed in the first pin hole for insertion into a first bone adjacent to the anatomical joint. The second clamp is slidingly disposed on the second shaft, the second clamp including a second pin hole. The second bone pin is disposed in the second pin hole for insertion into a second bone adjacent to the anatomical joint. The distraction screw is disposed between the threaded partial bore and the recess such that the distraction screw is threadedly engaged with the threaded partial bore and axially and radially retained by the recess. The first engagement feature cooperates with the second engagement feature to form a hinge joint with a single axis of rotation connecting the first shaft to the second shaft, the first shaft and the second shaft being constrained by the hinge joint to move relative to one another only around the single axis of rotation of the hinge joint. The first engagement feature includes a first locking feature and the second engagement feature includes a second locking feature such that when the reversible lock is engaged, the first locking feature and the second locking feature engage one another, preventing rotation about the single axis of rotation of the hinge joint. The first shaft, the second shaft, and the hinge joint are disposed in a single plane with the single axis of rotation of the hinge joint being about orthogonal to the single plane. The first bone pin is disposed in the first pin hole aligned about orthogonal to the single plane such that the first bone pin is aligned about parallel to the single axis of rotation of the hinge joint. The second bone pin is disposed in the second pin hole aligned about orthogonal to the single plane such that the second bone pin is aligned about parallel to the single axis of rotation of the hinge joint and the first bone pin. Clockwise rotation of the distraction screw advances the first clamp along the first shaft in a first direction and counterclockwise rotation of the distraction screw advanced the first clamp along the first shaft opposite to the first direction.

BRIEF DESCRIPTION OF THE DRAWINGS

Features and advantages of the general inventive concepts will become apparent from the following description made with reference to the accompanying drawings, including drawings represented herein in the attached set of figures, of which the following is a brief description.

Wherever possible, the same reference numbers will be used throughout the drawings to represent the same parts.

DETAILED DESCRIPTION

Figure 1:
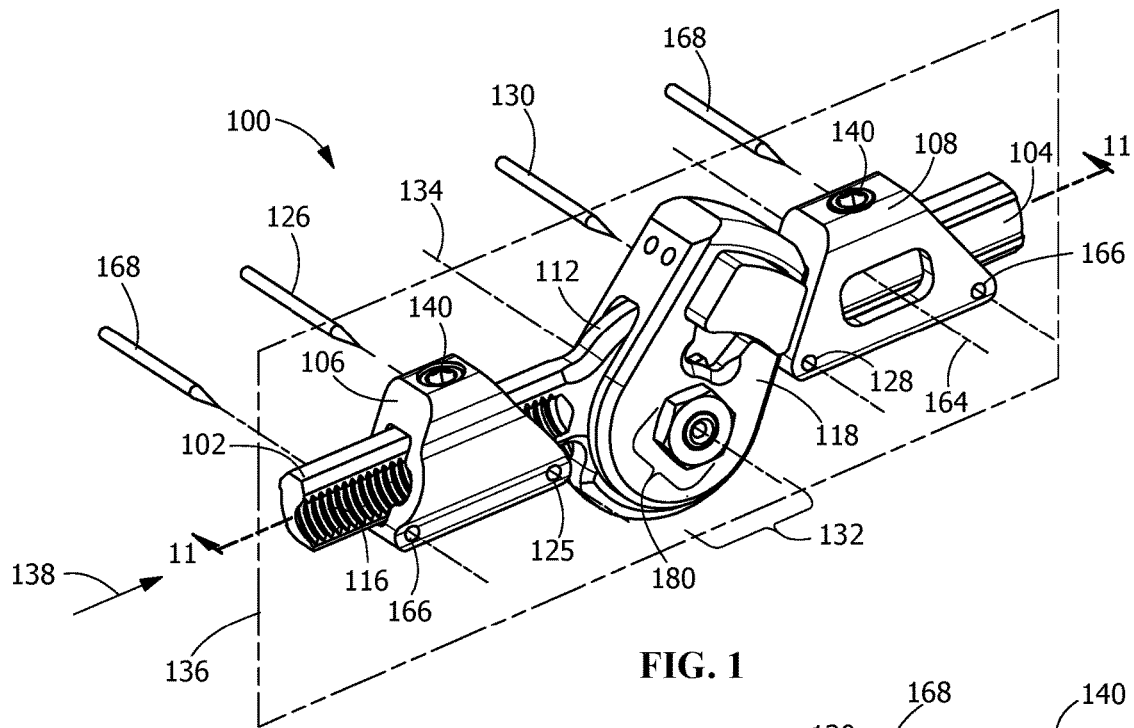
FIG. 1 is a top-front-right side perspective view of a monoplanar device, according to an embodiment of the present disclosure.
Figure 2:
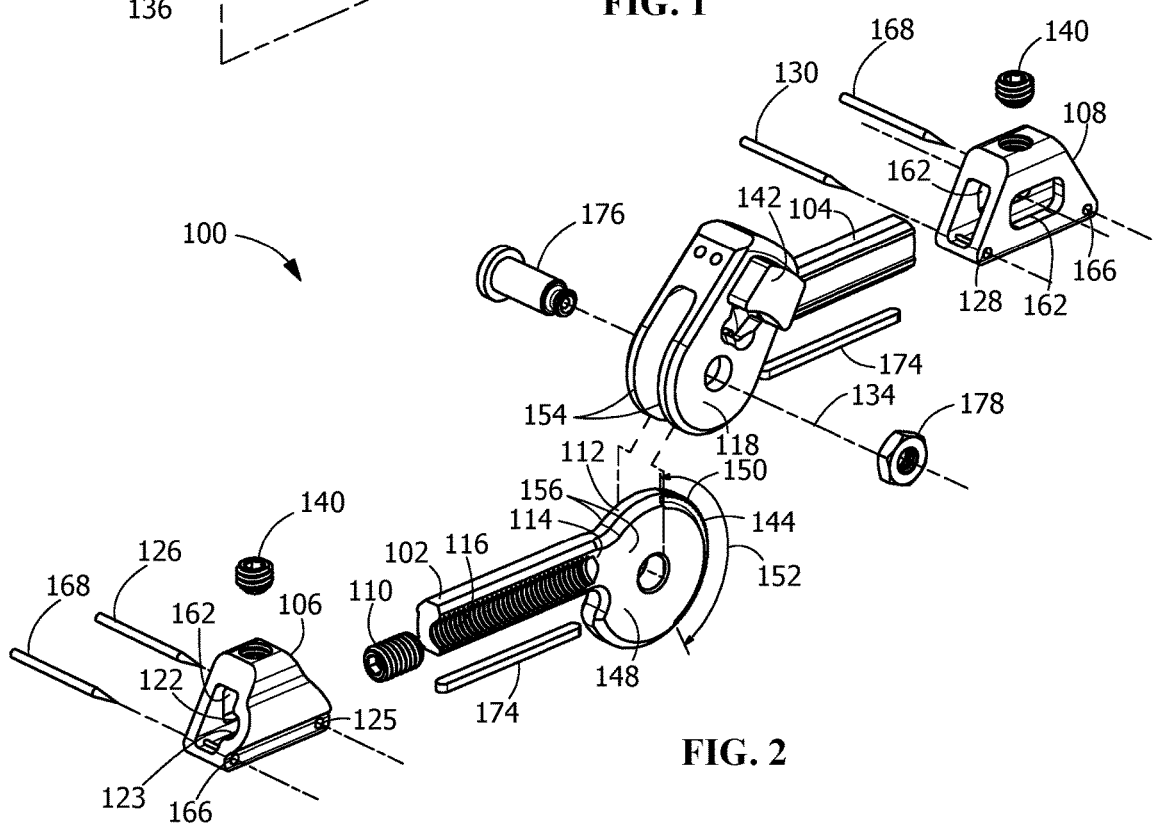
FIG. 2 is an exploded top-front-right side perspective view of the monoplanar device of FIG. 1, according to an embodiment of the present disclosure.
Figure 3:
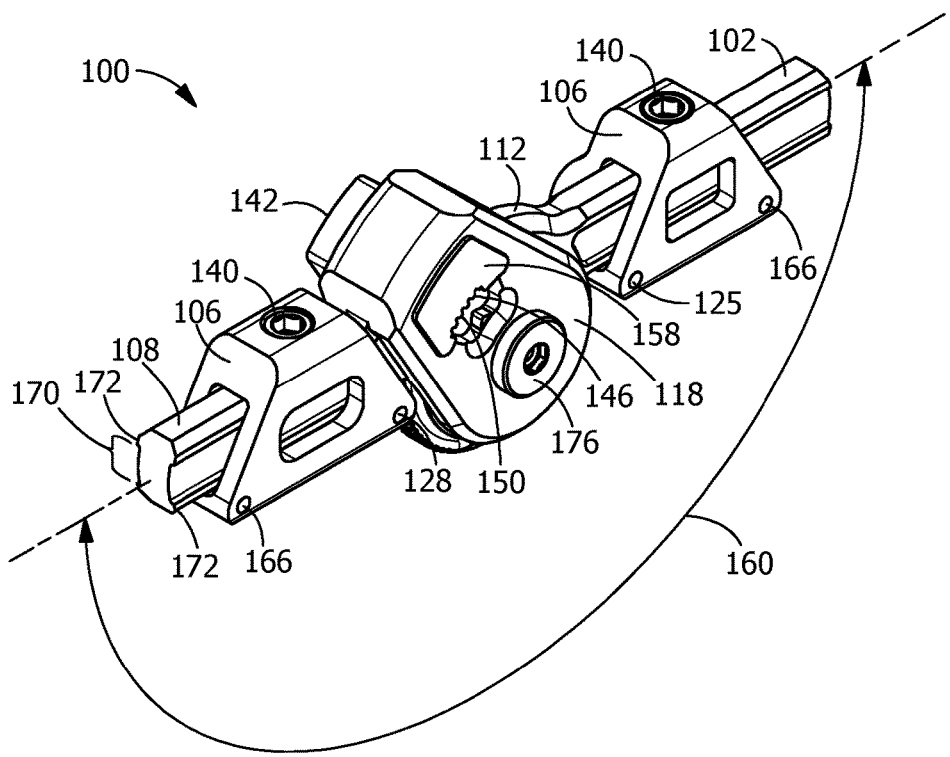
FIG. 3 is a top-rear-left side perspective view of the monoplanar device of FIG. 1, according to an embodiment of the present disclosure.
Figure 4:
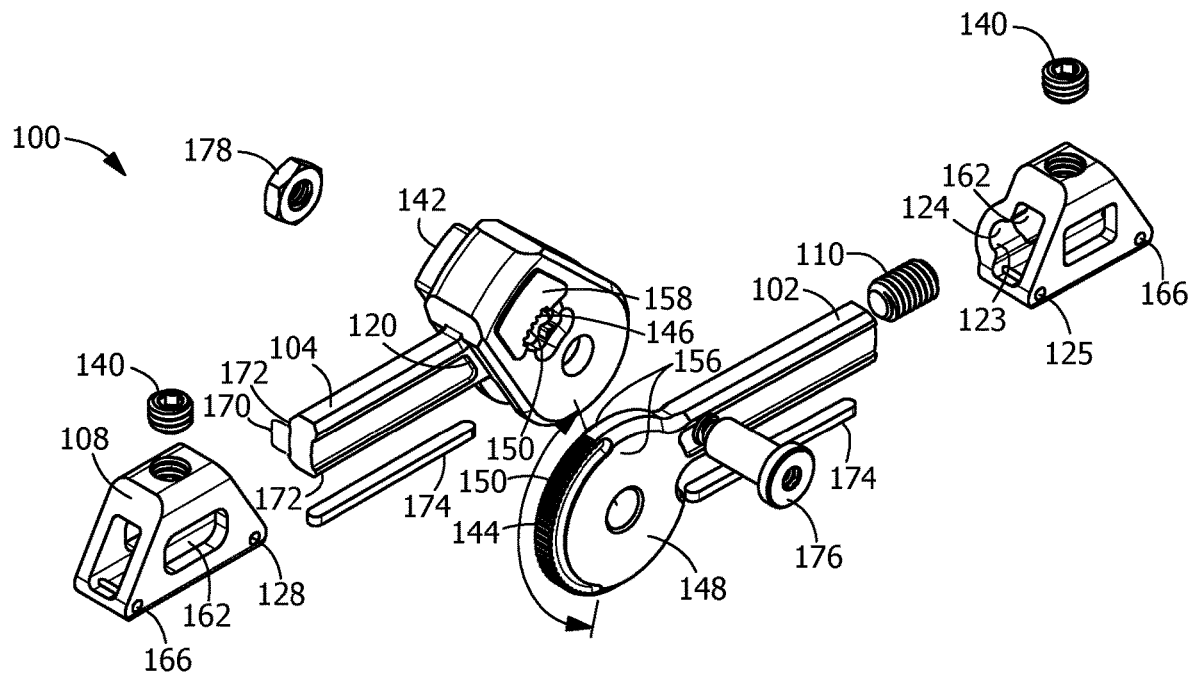
FIG. 4 is an exploded top-rear-left side perspective view of the monoplanar device of FIG. 1, according to an embodiment of the present disclosure.
Figure 5:
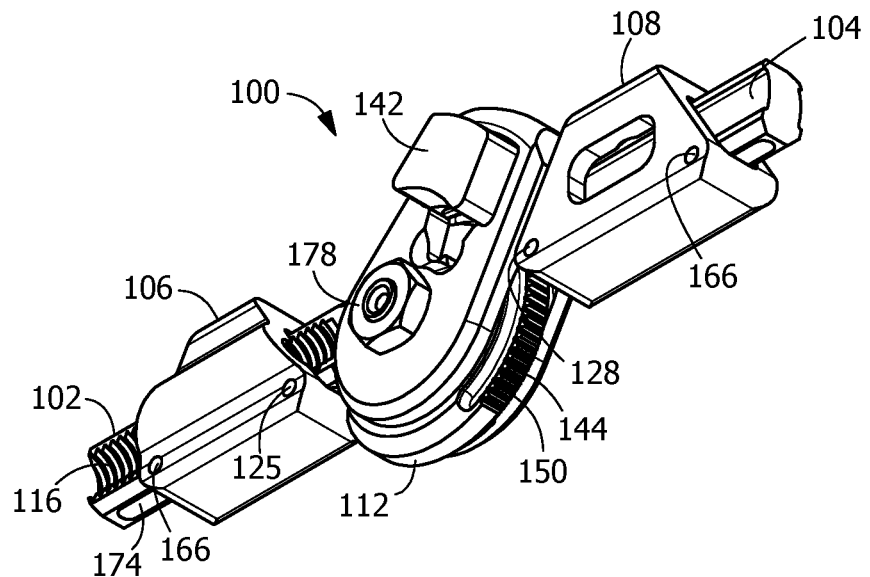
FIG. 5 is a bottom-rear-right side perspective view of the monoplanar device of FIG. 1, according to an embodiment of the present disclosure.
Figure 6:
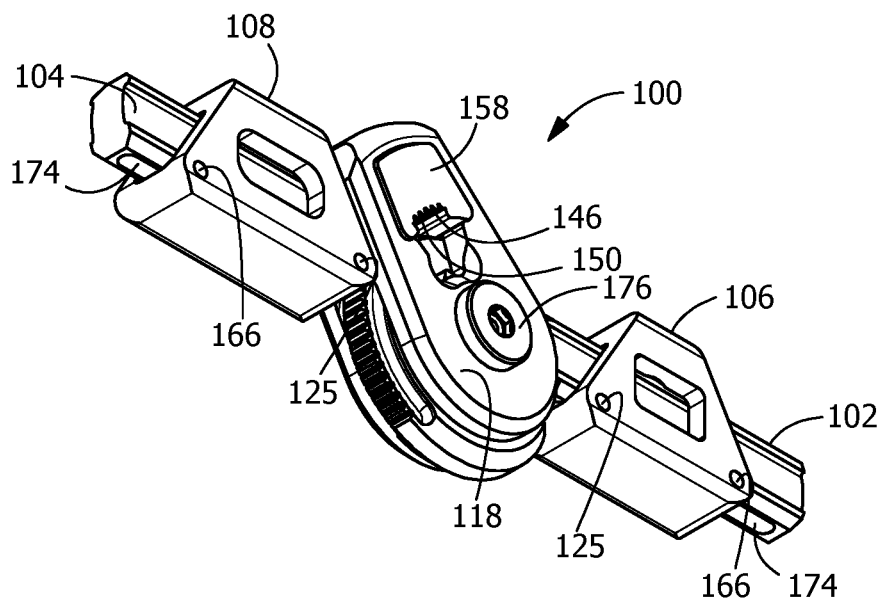
FIG. 6 is a bottom-front-left side perspective view of the monoplanar device of FIG. 1, according to an embodiment of the present disclosure.
Figure 7:
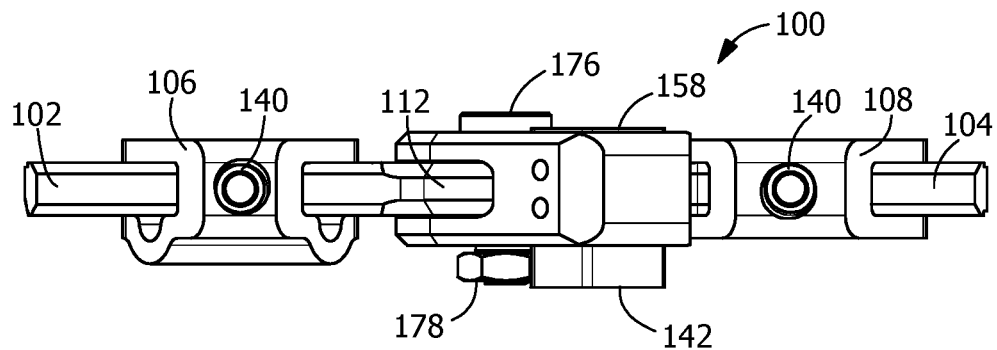
FIG. 7 is a top view of the monoplanar device of FIG. 1, according to an embodiment of the present disclosure.
Figure 8:
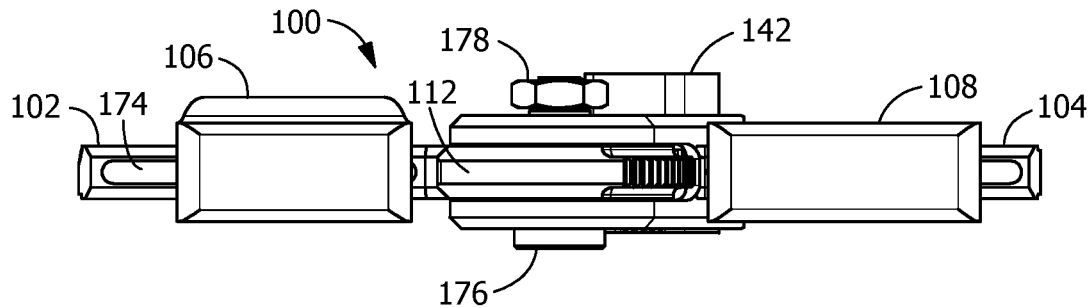
FIG. 8 is a bottom view of the monoplanar device of FIG. 1, according to an embodiment of the present disclosure.
Figure 9:
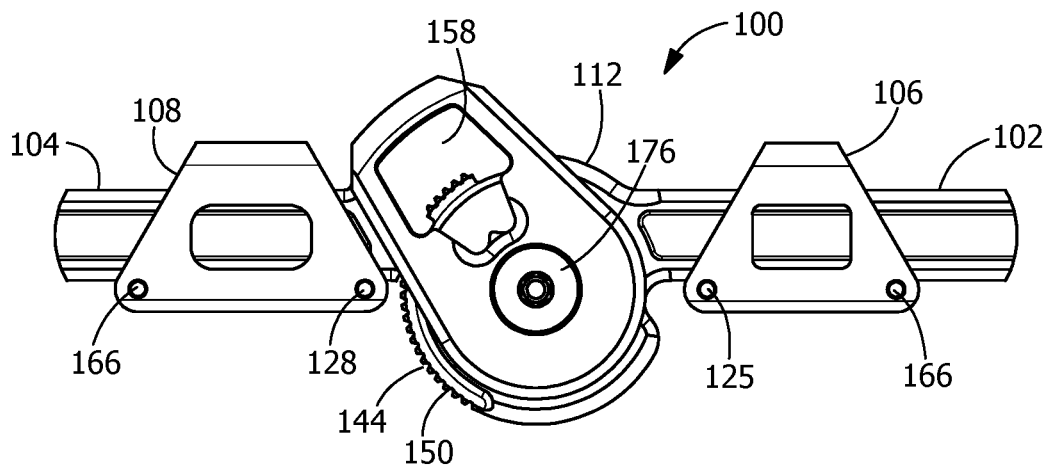
FIG. 9 is a left side view of the monoplanar device of FIG. 1, according to an embodiment of the present disclosure.
Figure 10:
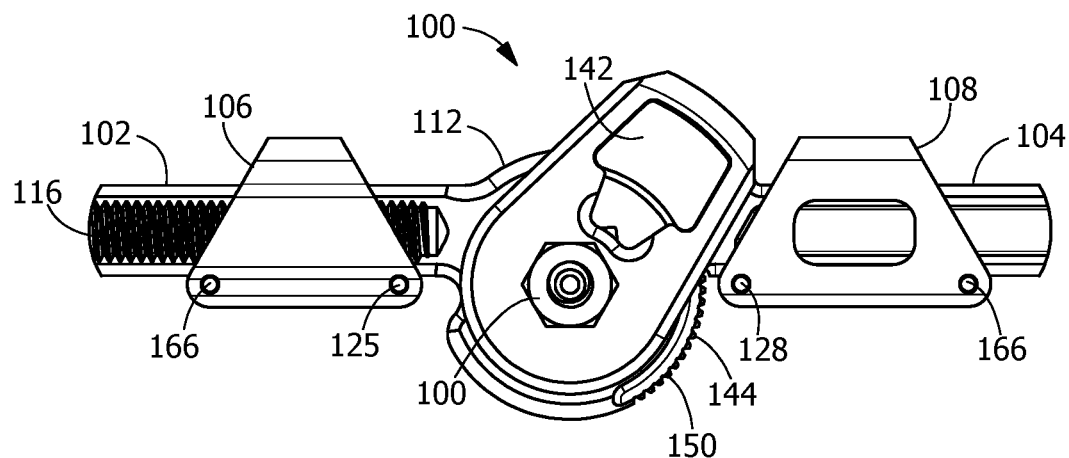
FIG. 10 is a right side view of the monoplanar device of FIG. 1, according to an embodiment of the present disclosure.
Figure 11:
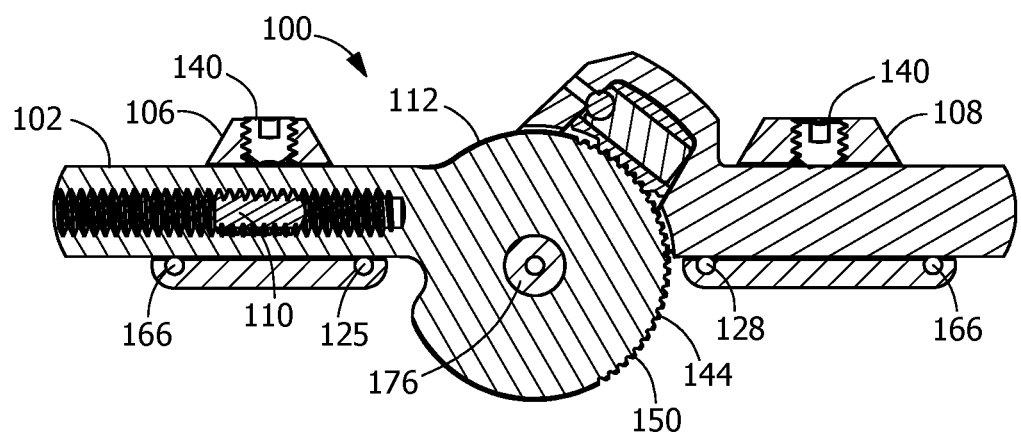
FIG. 11 is a right side cross-section view taken along lines 11-11 of the monoplanar device of FIG. 1, according to an embodiment of the present disclosure.

This disclosure describes exemplary embodiments in accordance with the general inventive concepts and is not intended to limit the scope of the invention in any way. Indeed, the invention as described in the specification is broader than and unlimited by the exemplary embodiments set forth herein, and the terms used herein have their full ordinary meaning.

The shortcomings in the art have been overcome by the instant invention which provides a hinged design based on the native joint axis to allow more anatomic mobilization of an affected joint and with minimal bulk to improve patient tolerance, improve precision, improve stability, improve distraction control, or combinations thereof.

Referring to FIGS. 1-15, in one embodiment, a monoplanar device 100 for stabilizing and distracting an anatomical joint 10 includes a first shaft 102, a second shaft 104, a first clamp 106, a second clamp 108, and a distraction screw 110.

The first shaft 102 includes a first engagement feature 112 disposed at a first end 114 of the first shaft 102 and a threaded partial bore 116 disposed along the first shaft 102. The second shaft 104 includes a second engagement feature 118 disposed at a first end 120 of the second shaft 104. The first clamp 106 is slidingly disposed on the first shaft 102, and the first clamp 106 includes a recess 122 and a first pin hole 125 arranged to receive a first bone pin 126 for insertion into a first bone 12 adjacent to the anatomical joint 10. The second clamp 108 is slidingly disposed on the second shaft 104, and the second clamp 108 includes a second pin hole 128 arranged to receive a second bone pin 130 for insertion into a second bone 14 adjacent to the anatomical joint 10. The distraction screw 110 is disposed between the threaded partial bore 116 and the recess 122 such that the distraction screw 110 is threadedly engaged with the threaded partial bore 116 and axially and radially retained by the recess 122. The distraction screw 110 may be axially retained by any suitable retention structure, including, but not limited to, a paired forward stop 123 and rearward stop 124 which extend from the recess 122 axially ahead and behind the distraction screw 110 such that the distraction screw 110 is axially held in place relative to the first claim 106.

The first engagement feature 112 cooperates with the second engagement 118 feature to form a hinge joint 132 with a single axis of rotation 134 connecting the first shaft 102 to the second shaft 104. The first shaft 102 and the second shaft 104 are constrained by the hinge joint 132 to move relative to one another only around the single axis of rotation 134 of the hinge joint 132. The first shaft 102, the second shaft 104, and the hinge joint 132 are disposed in a single plane 136 with the single axis of rotation 134 of the hinge joint 132 being about orthogonal to the single plane 136. The first pin hole 125 is aligned to receive the first bone pin 126 about orthogonal to the single plane 136 such that the first bone pin 126 is aligned about parallel to the single axis of rotation 134 of the hinge joint 132. The second pin hole 128 is aligned to receive the second bone pin 130 about orthogonal to the single plane 136 such that the second bone pin 130 is aligned about parallel to the single axis of rotation 134 of the hinge joint 132 and the first bone pin 126. As used herein, "about orthogonal" indicates within 5° of orthogonal in each dimension, and "about parallel" indicates within 5° of parallel.

Clockwise rotation of the distraction screw 110 advances the first clamp 106 along the first shaft 102 in a first direction 138 and counterclockwise rotation of the distraction screw 110 advanced the first clamp 106 along the first shaft 102 opposite to the first direction 138.

In one embodiment, the hinge joint 132 is a releasable hinge joint 132. As used herein, "releasable" indicates that that the hinge joint 132 may be disassembled without materially damaging any component of the monoplanar device 100. The hinge joint 132 may be secured with any suitable attachment mechanism 180, including, but not limited to, a bolt 176 and nut 178 attachment mechanism 180.

Each of the first clamp 106 and the second clamp 108 may include a set screw 140 disposed to lock the first clamp 106 or the second clamp 108 in position relative to the first shaft 102 or the second shaft 104 when tightened.

The monoplanar device 100 may further include a reversible lock 142. In one embodiment, the first engagement feature 112 includes a first locking feature 144 and the second engagement feature 118 includes a second locking feature 146 such that when the reversible lock 142 is engaged, the first locking feature 144 and the second locking feature 146 engage one another, preventing rotation about the single axis of rotation 134 of the hinge joint 132.

In one embodiment, the first engagement feature 112 is a discoid 148 in the single plane 136 and the first locking feature 144 is a plurality of ridges 150 running about orthogonal to the single plane 136 and disposed about a periphery 152 of the discoid 148, and the second engagement feature 118 is a pair of extensions 154 straddling lateral faces 156 of the discoid 148 and the second locking feature 146 includes at least one ridge 150 oriented to interlock with the plurality of ridges 150 of the first locking feature 144 when the reversible lock 142 is engaged. In another embodiment, the second engagement feature 118 is a discoid 148 in the single plane 136 and the second locking feature 146 is a plurality of ridges 150 running about orthogonal to the single plane 136 and disposed about a periphery 152 of the discoid 148, and the first engagement feature 112 is a pair of extensions 154 straddling lateral faces 156 of the discoid 148 and the first locking feature 144 includes at least one ridge 150 oriented to interlock with the plurality of ridges 150 of the second locking feature 146 when the reversible lock 142 is engaged.

Figure 12:
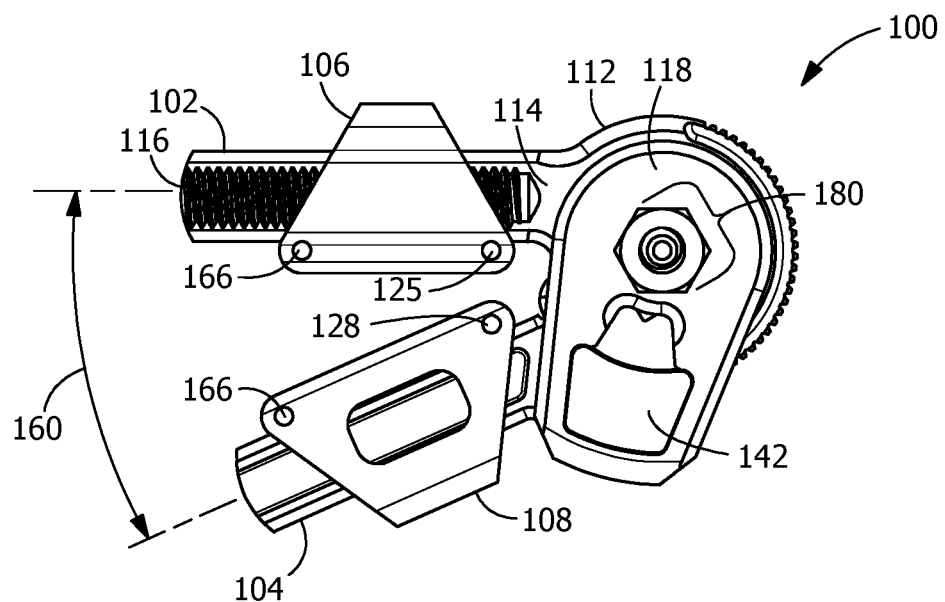
FIG. 12 is a right side view of the monoplanar device of FIG. 1 in a folded conformation about the single axis of rotation of the hinge joint, according to an embodiment of the present disclosure.
Figure 13:
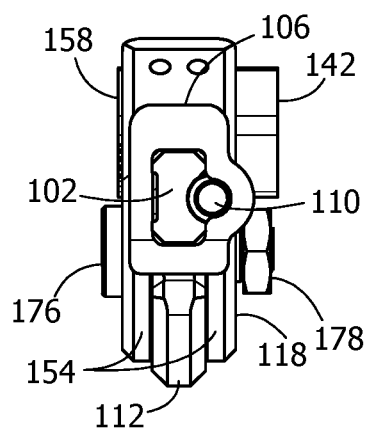
FIG. 13 is a front view of the monoplanar device of FIG. 1, according to an embodiment of the present disclosure.
Figure 14:
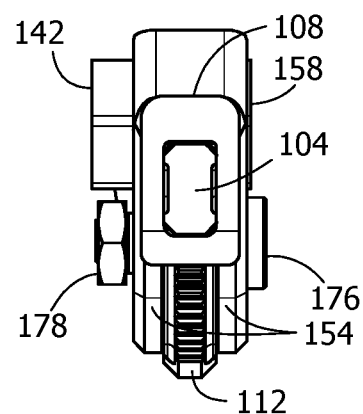
FIG. 14 is a rear view of the monoplanar device of FIG. 1, according to an embodiment of the present disclosure.
Figure 15:
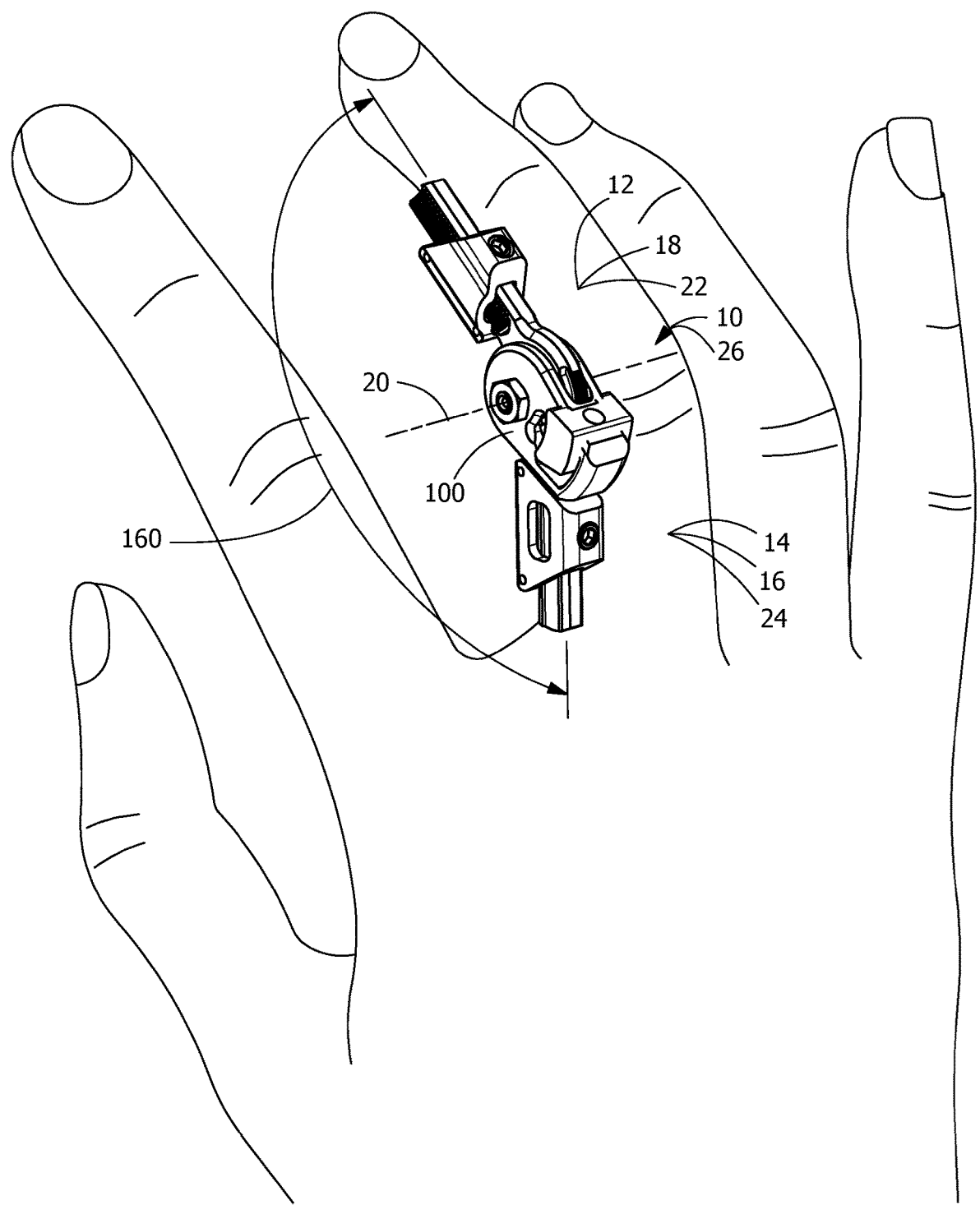
FIG. 15 is a schematic view of the monoplanar device of FIG. 1 affixed to a middle phalange and a proximal phalange of a proximal interphalangeal joint, according to an embodiment of the present disclosure.

The hinge joint 132 may include an angle gauge 158 displaying the relative angle 160 of the first shaft 102 to the second shaft 104 (as shown in FIG. 12). The angle gauge 158 may be analog or digital.

The first shaft 102 and the second shaft 104 may be formed of a radiopaque or a radiolucent material. Suitable radiopaque materials include, but are not limited to, metals, stainless steels, titanium, aluminum, other suitable medical grade metals, or combinations thereof. Suitable radiolucent materials include, but are not limited to, polymers, polyether ether ketone ("PEEK"), polyphenylsulfone ("PPSU," available from Solvay under the tradename RADEL), polyoxymethylene ("POM," available from Ensinger under the tradename ACETAL) or polyetherimide ("PEI," available from Sabic under the tradename ULTEM), other suitable medical grade polymer, or combinations thereof.

In one embodiment, wherein the first shaft 102 and the second shaft 104 are formed of a radiolucent material, the first shaft 102 and the second shaft 104 may further include a radiopaque marker for registering a position of the monoplanar device 100 radiographically when applied to the anatomical joint 10. Radiopaque markers may be formed from any suitable material, including, but not limited to, tantalum.

In one embodiment, wherein the first clamp 106 and the second clamp 108 are formed of a radiopaque material and the first shaft 102 and the second shaft 104 are formed of a radiolucent material, each of the first clamp 106 and the second clamp 108 includes radiovisualization apertures 162 disposed on each side of the first shaft 102 or the second shaft 104 such that a radiolucent imaging path 164 about orthogonal to the single plane 136 and passing through the first shaft 102 or the second shaft 104 is present through each of the first clamp 106 and the second clamp 108.

The first clamp 106 and the second clamp 108 may be formed of a radiopaque or a radiolucent material. In one embodiment, wherein the first clamp 106 and the second clamp 108 are formed of a radiolucent material, the first clamp 106 and the second clamp 108 include a radiopaque marker for registering a position of the monoplanar device 100 radiographically when applied to the anatomical joint 10.

Each of the first clamp 106 and the second clamp 108 may include any suitable number of additional pin holes 166 arranged to receive any suitable number of additional bone pins 168 about orthogonal to the single plane 136 and aligned about parallel to the single axis of rotation 134 of the hinge joint 132.

The monoplanar device 100 may further including a rotational limiter, wherein at least one of the first engagement feature 112 or the second engagement feature 118 includes at least one stop inhibiting rotation of the first shaft 102 and the second shaft 104 relative to one another around the single axis of rotation 134 of the hinge joint 132 beyond a predetermined range of rotation set by the at least one stop.

The rotational limiter may be an adjustable rotational limiter such that the position of the at least one stop is movable so as to increase or decrease the predetermined range of rotation.

In one embodiment, the monoplanar device 100 is adapted for fixation to a respective proximal bone 16 and a respective distal bone 18 at a joint axis 20 of an anatomical joint 10 between the respective proximal bone 16 and distal bone 18, with the single axis of rotation 134 of the hinge joint 132 aligned with the joint axis 20 between the respective proximal bone 16 and distal bone 18. Upon fixation of the monoplanar device 100 to the respective proximal bone 16 and distal bone 18 via insertion of the first bone pin 126 through the first pin hole 124 and the second bone pin 130 through the second pin hole 128 and into the respective proximal bone 16 and distal bone 18, rotation of the distraction screw 110 either distracts or compresses the respective proximal bone 16 and distal bone 18. Upon fixation of the monoplanar device 100 to the respective proximal bone 16 and distal bone 18, the monoplanar device 100 constrains the respective proximal bone 16 and distal bone 18 to move relative to one another only around the single axis of rotation 134 of the hinge joint 132. In a further embodiment, the monoplanar device 100 is adapted for fixation to a middle phalange 22 and a proximal phalange 24 of a proximal interphalangeal joint 26.

The first shaft 102, excluding the first engagement feature 112, and the second shaft 104, excluding the second engagement feature 118, may each include an axial web 170 in the single plane 136 disposed between two flanges 172 extending about perpendicular to the single plane 136.

The first clamp 106 and the second clamp 108 may each gave a trapezoidal shape in the single plane 136.

The monoplanar device 100 may include one or more inserts 174 disposed between the first shaft 102 and the first clamp 106, or between the second shaft 104 and the second clamp 108.

As used herein, the singular forms "a," "an," and "the" are intended to include the plural forms as well, unless the context clearly indicates otherwise. Anatomical references as used herein are intended to have the standard meaning for such terms as understood in the medical community. For example, the application may include reference to the following terms: volar (the front, as opposed to the back); dorsal (the back or behind, as opposed to the front); inferior (below, as opposed to superior); superior (above, as opposed to inferior); lateral (toward the left or right side of the body, as opposed to toward the middle); medial (in or toward the middle or inside of the body, as opposed to away from toward the left or right); proximal (toward the body, as opposed to toward the ends, such as of the fingers and hands); and distal (away from the body, as opposed to towards the body).

Unless otherwise indicated, all numbers expressing quantities, properties, and so forth as used in the specification and claims are to be understood as being modified in all instances by the term "about." Accordingly, unless otherwise indicated, the numerical properties set forth in the specification and claims are approximations that may vary depending on the suitable properties desired in embodiments of the present invention. Notwithstanding that any numerical ranges and parameters setting forth the broad scope of the general inventive concepts are approximations, numerical values set forth in the specific examples are reported as precisely as possible. Any numerical values, however, inherently contain certain errors necessarily resulting from error found in their respective measurements.

While various inventive aspects, concepts and features of the general inventive concepts are described and illustrated herein in the context of various exemplary embodiments, these various aspects, concepts and features may be used in many alternative embodiments, either individually or in various combinations and sub-combinations thereof. Unless expressly excluded herein all such combinations and sub-combinations are intended to be within the scope of the general inventive concepts.

Those skilled in the art may readily adopt one or more of the inventive aspects, concepts or features into additional embodiments and uses within the scope of the general inventive concepts even if such embodiments are not expressly disclosed herein. Moreover, while various aspects, features and concepts may be expressly identified herein as being inventive or forming part of an invention, such identification is not intended to be exclusive, but rather there may be inventive aspects, concepts and features that are fully described herein without being expressly identified as such or as part of a specific invention. Descriptions of exemplary methods or processes are not limited to inclusion of all steps as being required in all cases, nor is the order that the steps are presented to be construed as required or necessary unless expressly so stated. Further, while disclosed benefits, advantages, and solutions to problems have been described with reference to specific embodiments, these are not intended to be construed as essential or necessary to the invention.

What is claimed is:

1. A monoplanar device for stabilizing and distracting an anatomical joint comprising:
   a first shaft including a first engagement feature disposed at a first end of the first shaft and a threaded partial bore disposed along the first shaft;
   a second shaft including a second engagement feature disposed at a first end of the second shaft;
   a first clamp slidingly disposed on the first shaft, the first clamp including a recess and a first pin hole arranged to receive a first bone pin for insertion into a first bone adjacent to the anatomical joint;
   a second clamp slidingly disposed on the second shaft, the second clamp including a second pin hole arranged to receive a second bone pin for insertion into a second bone adjacent to the anatomical joint; and
   a distraction screw disposed between the threaded partial bore and the recess such that the distraction screw is threadedly engaged with the threaded partial bore and axially and radially retained by the recess,
   wherein the first engagement feature cooperates with the second engagement feature to form a hinge joint with a single axis of rotation connecting the first shaft to the second shaft, the first shaft and the second shaft being constrained by the hinge joint to move relative to one another only around the single axis of rotation of the hinge joint,
   wherein:
      the first shaft, the second shaft, and the hinge joint are disposed in a single plane with the single axis of rotation of the hinge joint being about orthogonal to the single plane;
      the first pin hole is aligned to receive the first bone pin about orthogonal to the single plane such that the first bone pin is aligned about parallel to the single axis of rotation of the hinge joint; and
      the second pin hole is aligned to receive the second bone pin about orthogonal to the single plane such that the second bone pin is aligned about parallel to the single axis of rotation of the hinge joint and the first bone pin, and
   wherein clockwise rotation of the distraction screw advances the first clamp along the first shaft in a first direction and counterclockwise rotation of the distraction screw advances the first clamp along the first shaft opposite to the first direction.

2. The monoplanar device of claim 1, wherein the hinge joint is a releasable hinge joint.

3. The monoplanar device of claim 1, wherein each of the first clamp and the second clamp includes a set screw disposed to lock the first clamp or the second clamp in position relative to the first shaft or the second shaft when tightened.

4. The monoplanar device of claim 1, further including a reversible lock, wherein the first engagement feature includes a first locking feature and the second engagement feature includes a second locking feature such that when the reversible lock is engaged, the first locking feature and the second locking feature engage one another, preventing rotation about the single axis of rotation of the hinge joint.

5. The monoplanar device of claim 4, wherein the first engagement feature is a discoid in the single plane and the first locking feature is a plurality of ridges running about orthogonal to the single plane and disposed about a periphery of the discoid, and the second engagement feature is a pair of extensions straddling lateral faces of the discoid and the second locking feature includes at least one ridge oriented to interlock with the plurality of ridges of the first locking feature when the reversible lock is engaged.

6. The monoplanar device of claim 4, wherein the second engagement feature is a discoid in the single plane and the second locking feature is a plurality of ridges running about orthogonal to the single plane and disposed about a periphery of the discoid, and the first engagement feature is a pair of extensions straddling lateral faces of the discoid and the first locking feature includes at least one ridge oriented to interlock with the plurality of ridges of the second locking feature when the reversible lock is engaged.

7. The monoplanar device of claim 1, wherein the hinge joint includes an angle gauge displaying the relative angle of the first shaft to the second shaft.

8. The monoplanar device of claim 1, wherein the first shaft and the second shaft are formed of a radiolucent material.

9. The monoplanar device of claim 8, wherein the first shaft and the second shaft include a radiopaque marker for registering a position of the device radiographically when applied to the anatomical joint.

10. The monoplanar device of claim 8, wherein the first clamp and the second clamp are formed of a radiopaque material, and each of the first clamp and the second clamp includes radiovisualization apertures disposed on each side of the first shaft or the second shaft such that a radiolucent imaging path about orthogonal to the single plane and passing through the first shaft or the second shaft is present through each of the first clamp and the second clamp.

11. The monoplanar device of claim 1, wherein the first clamp and the second clamp are formed of a radiolucent material.

12. The monoplanar device of claim 11, wherein the first clamp and the second clamp include a radiopaque marker for registering a position of the device radiographically when applied to the anatomical joint.

13. The monoplanar device of claim 1, wherein each of the first clamp and the second clamp includes an additional pin hole arranged to receive an additional bone pin about orthogonal to the single plane and aligned about parallel to the single axis of rotation of the hinge joint.

14. The monoplanar device of claim 1, further including a rotational limiter, wherein at least one of the first engagement feature or the second engagement feature includes at least one stop inhibiting rotation of the first shaft and the second shaft relative to one another around the single axis of rotation of the hinge joint beyond a predetermined range of rotation set by the at least one stop.

15. The monoplanar device of claim 14, wherein the rotational limiter is an adjustable rotational limiter such that the position of the at least one stop is movable so as to increase or decrease the predetermined range of rotation.

16. The monoplanar device of claim 1, wherein:
the monoplanar device is adapted for fixation to respective proximal bone and distal bone at a joint axis between the respective proximal bone and distal bone with the single axis of rotation of the hinge joint aligned with the joint axis between the respective proximal bone and distal bone;
upon fixation of the monoplanar device to the respective proximal bone and distal bone via insertion of the first bone pin through the first pin hole and the second bone pin through the second pin hole and into the respective proximal bone and distal bone, rotation of the distraction screw either distracts or compresses the respective proximal bone and distal bone; and
upon fixation of the monoplanar device to the respective proximal bone and distal bone, the monoplanar device constrains the respective proximal bone and distal bone to move relative to one another only around the single axis of rotation of the hinge joint.

17. The monoplanar device of claim 16, wherein the monoplanar device is adapted for fixation to a middle phalange and a proximal phalange of a proximal interphalangeal joint.

18. The monoplanar device of claim 1, wherein the first shaft, excluding the first engagement feature, and the second shaft, excluding the second engagement feature, each includes an axial web in the single plane disposed between two flanges extending about perpendicular to the single plane.

19. The monoplanar device of claim 1, wherein the first clamp and the second clamp each has a trapezoidal shape in the single plane.

20. A monoplanar device for stabilizing and distracting an anatomical joint comprising:
a first shaft including a first engagement feature disposed at a first end of the first shaft and a threaded partial bore disposed along the first shaft;
a second shaft including a second engagement feature disposed at a first end of the second shaft;
a first clamp slidingly disposed on the first shaft, the first clamp including a recess and a first pin hole;
a first bone pin disposed in the first pin hole for insertion into a first bone adjacent to the anatomical joint;
a second clamp slidingly disposed on the second shaft, the second clamp including a second pin hole;
a second bone pin disposed in the second pin hole for insertion into a second bone adjacent to the anatomical joint;
a distraction screw disposed between the threaded partial bore and the recess such that the distraction screw is threadedly engaged with the threaded partial bore and axially and radially retained by the recess; and
a reversible lock,
wherein the first engagement feature cooperates with the second engagement feature to form a hinge joint with a single axis of rotation connecting the first shaft to the second shaft, the first shaft and the second shaft being constrained by the hinge joint to move relative to one another only around the single axis of rotation of the hinge joint,
wherein the first engagement feature includes a first locking feature and the second engagement feature includes a second locking feature such that when the reversible lock is engaged, the first locking feature and the second locking feature engage one another, preventing rotation about the single axis of rotation of the hinge joint,
wherein:
the first shaft, the second shaft, and the hinge joint are disposed in a single plane with the single axis of rotation of the hinge joint being about orthogonal to the single plane;
the first bone pin is disposed in the first pin hole aligned about orthogonal to the single plane such that the first bone pin is aligned about parallel to the single axis of rotation of the hinge joint; and
the second bone pin is disposed in the second pin hole aligned about orthogonal to the single plane such that the second bone pin is aligned about parallel to the single axis of rotation of the hinge joint and the first bone pin, and
wherein clockwise rotation of the distraction screw advances the first clamp along the first shaft in a first direction and counterclockwise rotation of the distraction screw advances the first clamp along the first shaft opposite to the first direction.

* * * * *